(12) United States Patent
Gattinoni

(10) Patent No.: US 6,461,315 B1
(45) Date of Patent: Oct. 8, 2002

(54) APPARATUS FOR IMPROVING THE DISTRIBUTION OF GAS IN THE LUNGS OF A PATIENT RECEIVING RESPIRATORY TREATMENT

(75) Inventor: Luciano Gattinoni, Milan (IT)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/268,779

(22) Filed: Mar. 16, 1999

(30) Foreign Application Priority Data

Mar. 16, 1998 (SE) .............................. 9800855

(51) Int. Cl.[7] .............................................. A61H 31/00
(52) U.S. Cl. ........................... 601/41; 601/44; 601/152; 128/204.21
(58) Field of Search ............................. 601/41–44, 117, 601/108, 136, 152; 128/204.18, 204.23, 204.21

(56) References Cited

U.S. PATENT DOCUMENTS 3,509,899 A * 5/1970 Hewson
3,552,390 A * 1/1971 Muller
3,965,893 A   6/1976 Ragailler
4,424,806 A   1/1984 Newman et al.
4,570,615 A * 2/1986 Barkalow
4,676,232 A   6/1987 Olsson et al.
4,928,674 A * 5/1990 Halperin et al.
5,806,512 A * 9/1998 Abramov et al.

FOREIGN PATENT DOCUMENTS

SE          87787      11/1936
SE         147344      10/1954

* cited by examiner

*Primary Examiner*—Danton D. DeMille
(74) *Attorney, Agent, or Firm*—Schiff Hardin & Waite

(57) ABSTRACT

When treating patients with severely injured or sick lungs, there is often the problem of providing a life sustaining treatment without risking further damage to the lungs as a result of the treatment itself. An apparatus for improving the distribution of gas in the lungs of a patient to alleviate this problem directs a controllable pressure to one or several selected positions on the patient's thorax. In one embodiment of the apparatus, the apparatus includes a vest which includes compartments which can be filled with a fluid under pressure from a pressure source via tubes.

11 Claims, 3 Drawing Sheets

APPARATUS FOR IMPROVING THE DISTRIBUTION OF GAS IN THE LUNGS OF A PATIENT RECEIVING RESPIRATORY TREATMENT

BACKGROUND OF THE INVENTION

1. Field of the Invention

The present invention is directed to an apparatus for improving the distribution of gas in the lungs of a patient during respiratory treatment.

2. Description of the Prior Art

Respiratory treatment is vital for many patients and has saved many lives over the years. The equipment, i.e. ventilators and respirators, has been developed to be able to supply a number of different respiration modes with a high accuracy of the supplied pressure and volume of breathing gas.

When treating patients with severely ill (through sickness or injury) lungs, there is often the problem of providing a life sustaining treatment without risking damage to the lungs caused by the treatment itself.

For many of these patients physicians are reluctant in providing pressures higher than 35 $cmH_2O$, as this was a limit proposed at a consensus conference in 1994. This pressure limit is intended for transmural pressure, but is sometimes misinterpreted as the peak inspiratory pressure.

The tidal volume for patients with severely sick or injured lungs is often very small, and may for an adult be as low as the tidal volume of a baby (hence the expression baby lung syndrome)

Due to the condition of the lung, the pressure within different compartments of the lung may vary considerably and some compartments or clusters of alveoli may be collapsed.

A collapsed alveolus can be compared to a balloon. It requires a high pressure even to make it begin to inflate (open up), but once its been opened up, a lower pressure is sufficient for further inflation. If the required pressure is supplied from a ventilator, other parts of the lung may be exposed to pressures that might cause overdistention (disrupting the important exchange of gas between the lungs and the circulatory system) or even barotrauma.

When supplying breathing gas to the patient at a pressure which will not damage the lung, the gas will most likely be distributed only to healthy parts of the lungs. This may cause the sick or injured parts of the lungs to deteriorate further.

The gas exchange between the lungs and the circulatory system is better at the lower part of the lungs, close to the diaphragm. This is due to a better blood perfusion in these parts of the lungs. Since these parts are the most remote from the ventilator (or trachea) it takes more time for the gases in these lower parts to be transported out of the lungs and replaced with fresh gas. It would be beneficial to the patient, if the lower parts of the lungs could receive sufficient ventilation.

It is therefore important to obtain an even distribution of supplied breathing gas in the lungs.

Most patients are placed in a supine position during treatment. Visual monitoring of the patients condition by the staff, as well as access for other equipment, such as infusion apparatus, EGG apparatus, EEC apparatus, etc. is much better when the patient is in the supine position.

Experiments have shown that as many as 70% of patients with acute lung injury have improved gas exchange if they are placed in a prone position. The reason for this is believed to be an improved distribution of gas from the upper part of the lungs to the lower parts of the lungs, due to a decrease in chest wall compliance.

As already stated, placing patients in a prone position is very impractical and may even impede other treatment.

SUMMARY OF THE INVENTION

An object of the present invention is to provide an apparatus which can be used for obtaining a more even distribution of gas in the lungs.

The above object is achieved in accordance with the principles of the present invention in an apparatus including a respiratory assist device connected to the airways of a patient for supplying gas to the airways, and an extracorporeal gas distribution arrangement which directs a controllable pressure to one or more selected extracorporeal positions on the patient's thorax synchronized with the supply of respiratory gas from the respiratory assist device.

The extracorporeal gas distribution arrangement can include one or more pressure-applying elements adapted for placement at selected positions on the patient's thorax, a force generating unit which generates a controllable force, and a force-directing arrangement, connected between the force generating unit and the force applying elements, for conveying or directing the force generated by the force generating unit to one or more of the force applying elements.

Basically, the apparatus according to the invention needs only be adapted to provide a pressure, or a force on one or several specific positions on the patient's chest, preferably on the upper part of the chest, on each side of the sternum (breastbone). Naturally, the patient should be in a position which provides access to the chest. In its simplest construction, the apparatus may even consist of a weight, shaped to be securely placed on the patient's chest. This would, however, require more staff for handling the apparatus. The more preferred embodiments, described below, do not need the same supervision from the staff.

By providing a sufficient pressure of the chest wall by means of the apparatus, the transmural pressure gradient in the lungs can be decreased, indicating that higher peak inspiratory pressures can be used. Thus, not only will the distribution of gas be improved, but higher peak pressures can also be supplied from a ventilator or respirator without increasing the risk of damaging the lungs.

It should be noted that the apparatus according to the invention is different from known CPR-apparatus, which include some kind of means for providing heart massage by applying force on or near the sternum, above the heart. CPR is used when the heart has stopped and thus presents a completely different situation. The CPR systems are therefore not suitable for improving the distribution of gas in the lungs.

In U.S. Pat. No. 4,676,232 a system for promoting blood circulation is described. This system basically comprises a device which encloses the patient's chest and abdomen. The device prevents the chest and abdomen from expanding during respiration, thereby forcing the lungs to expand "inwardly", in particular against the heart. By correlating respiration phases with heart beats, the pressure on the heart will increase, resulting in an increase in stroke volume of the heart.

In similarity with systems for providing respiration by enclosures around chest and abdomen, this known system is not suitable for improving the distribution of gas in the lungs.

For the apparatus according to the invention, it is most beneficial to supply the pressure synchronized with inspiration phases, during which the pressure applied on the chest could be varied according to predetermined patterns. Any such pattern could be set by a physician before onset of inspiration, or be controlled by the physician during inspiration. Automation is also possible, if the gas pressure within the lung is measured at several locations within the lungs, or by obtaining measurements reflecting the transmural pressure.

During expiration, the pressure is preferably removed to allow normal exhalation from the patient. It should be noted, however, that for some disease groups it might be beneficial if pressure were delivered during expiration as well, e. g. as a continuous positive pressure.

It is not necessary to apply the pressure during each respiratory cycle.

The preferred embodiments of the apparatus according to the invention can have numerous shapes, all suitable for applying the pressure in a controlled and safe manner.

In one embodiment of the invention, an arm is arranged over the bed, holding one or several mechanical actuators which can be brought into contact with the chest for supplying the pressure. The actuators could be bellows-shaped and pneumatically controlled, or telescopic and hydraulically controlled, or even a combination. The force can also be produced by means of springs, pistons, gears or any other mechanical means. A very simple but effective alternative, is to use a weight as actuator. The pressure is applied either by lowering the arm towards the chest, or by lowering the weight (by strings or similar means).

The actuator could be an integrated part of the arm, whereby both parts move in order to supply the pressure. The arm is therefore preferably made to be freely positionable in a number of positions for facilitating the positioning of the actuators on the chest.

In another embodiment a support in the shape of an arc above the patient is used instead of the arm. The actuator could basically be any of the actuators mentioned above.

In a third embodiment an inflexible cover is placed across the chest. The cover has compartments which are utilized for generating the pressure on the chest. Basically, the cover could be a cloth, which is draped across the chest. The compartments above the positions to be pressurized could be filled with solid elements, for instance rubber. A system for tightening the cloth pulls the cloth tighter across the chest when the pressure is to be applied, whereby the elements will be pressed against the proper places on the chest.

In the alternative, a pneumatic or hydraulic fluid system could be used for causing the elements to press against the chest with the controllable pressure.

In another embodiment, the cover is made as a vest, which is 20 worn by the patient. The vest includes compartments which can be pressurized by fluids, preferably a gas.

The vest could also consist of a back plate, placed under the patient, and a front piece, which is securely strapped to the back plate at the sides of the patient.

Different combinations of the disclosed alternatives is also possible, where applicable.

Care should be taken not to expose the chest to too much strain or monotonous load. In particular, bed sores should be avoided by selecting proper application of the pressure. One way of doing this is to somewhat vary the position between each pressure cycle.

DESCRIPTION OF THE PREFERRED EMBODIMENTS

Figure 1:
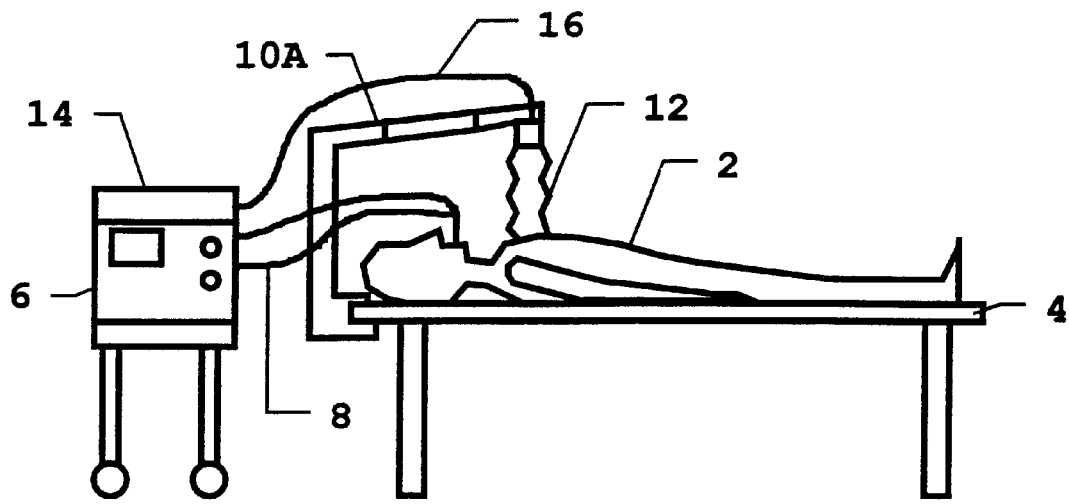
FIG. 1 shows a first embodiment of the apparatus according to the invention.

In FIG. 1 a patient 2 is shown lying on a hospital bed 4. The patient 2 is connected to a ventilator 6 via a tubing system 8 for receiving respiratory treatment.

Figure 2:
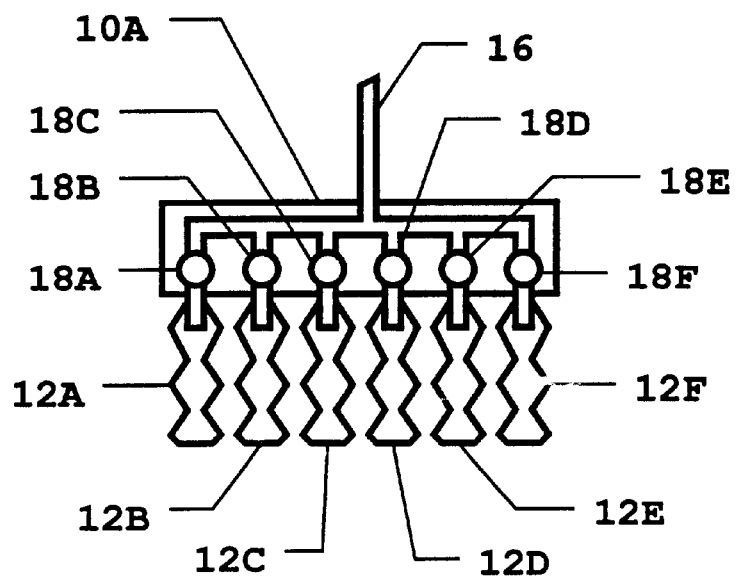
FIG. 2 shows a detail of the apparatus according to the first embodiment.

In order to improve the gas distribution within the lungs, and thereby improving the gas exchange between the lungs and the circulatory system, an apparatus is provided for producing a controllable pressure on selected positions on the chest of the patient 2. The apparatus includes a support 10A in the shape of an arm, which is firmly fixed to the bed and stretches over the head and chest of the patient 2. A bellows system 12, which is described in greater detail in connection with FIG. 2 below, can be placed at selected positions on the chest, preferably on the upper part of the chest, and with a small inclination from the breastbone. Pressurized gas is supplied from a gas source 14 via a tube 16 to the bellows system 12 at the onset of an inspiration phase. This is controlled by using the control signal from the ventilator 6 itself.

The supplied pressure can vary during the inspiration in any selected manner, depending on the condition of the patient 2 etc. The supplied pressure will cause the breathing gas supplied from the ventilator 6 to become more evenly distributed in the lungs, in particular toward the lower parts of the lung.

The bellows system 12 contains (FIG. 2) in this embodiment six bellows 12A, 12B, 12C, 12D, 12E, 12F, all connected to the arm 10 and the tube 16. By controlling valves 18A, 18B, 18C, 18D, 18E, 18F which respectively separate the bellows 12A, 12B, 12C, 12D, 12E, 12F from the tube 16, any selectable number of these bellows car be filled with gas for supplying the desired pressure. By varying the positions in this manner, bed sores can be effectively avoided, even if pressure is supplied at each inspiration phase.

Figure 3:
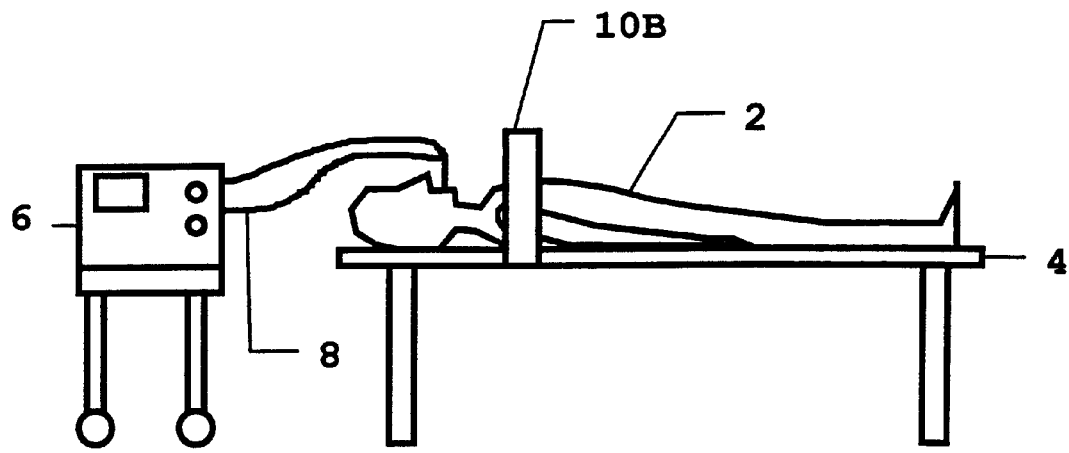
FIG. 3 shows a second embodiment of the apparatus according to the invention.
Figure 4:
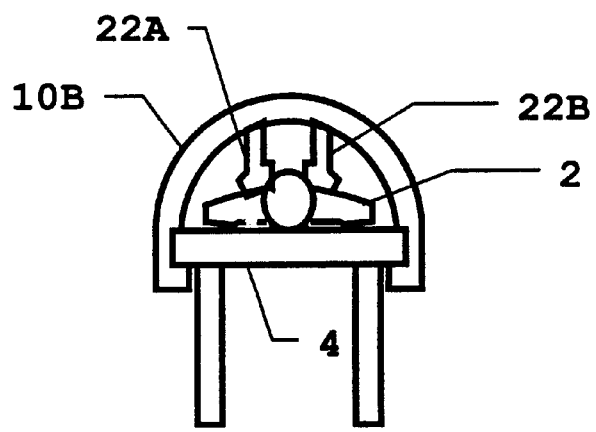
FIG. 4 shows a detail of the apparatus according to the second embodiment.

In FIGS. 3 and 4 a second embodiment of the apparatus is shown. In this case, the apparatus has a support 10B in the shape of an arc above the patient 2. The arc 10B is firmly attached to the bed 4, as can be seen more clearly in FIG. 4.

From the arc 10B, two piston-like actuators 22A, 22B are situated. The actuators 22A, 22B can be moved along the arc 10B in order to be positioned suitably at selected positions on the chest of the patient 2. The actuators 22A, 22B are positioned, so that they are activated to exert pressure on the chest in response to chest movements indicating the onset of an inspiration. The actuators 22A, 22B are equipped with pressure sensors for this purpose (not shown).

Figure 5:
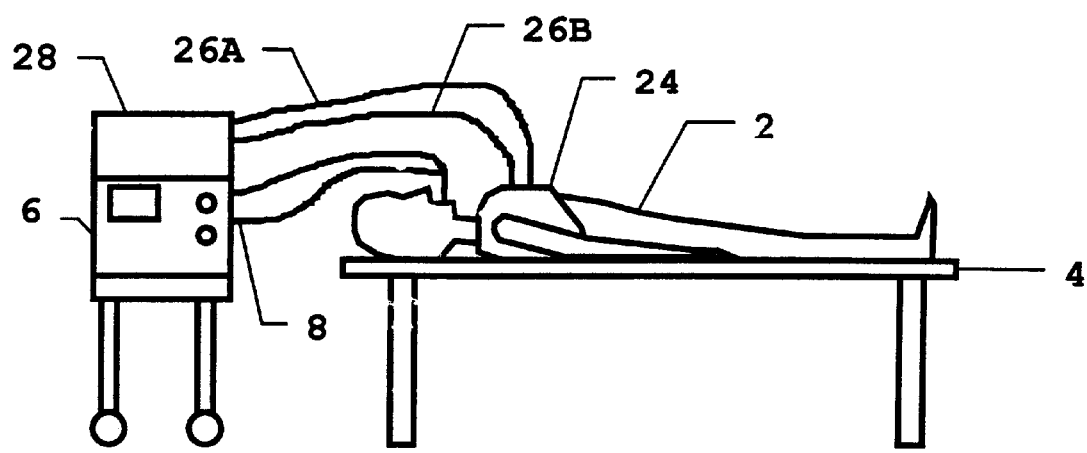
FIG. 5 shows a third embodiment of the apparatus according to the invention.
Figure 6:
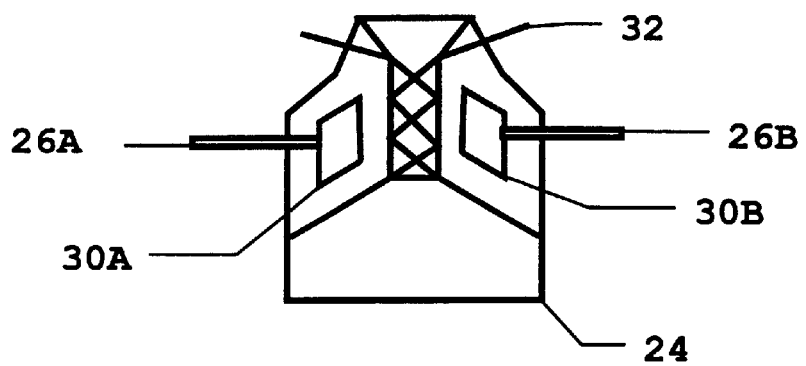
FIG. 6 shows a detail of the apparatus according to the third embodiment.

In FIGS. 5 and 6 a third embodiment of the apparatus is shown. In this embodiment the apparatus is in the form of a vest 24, which is placed on the patient 2. The vest includes in this case two compartments 30A, 30B which can be selectively filled with pressurized fluid, preferably gas, via gas tubes 26A, 26B from a gas source 28. The vest 24 can be tightened on the patient 2 by a strap 32. The vest 24 is made of an inelastic, strong material to ensure that the pressure is directed to the chest.

The vest 24 could alternatively can be made to of two parts, a back piece, namely which is placed under the patient (and which may even constitute an integral part of the bed), and a front piece, which is placed on the chest and attached to the back piece on both sides, e. g. with straps.

The vest can also have several compartments, each fillable with a pressurized fluid. Each compartment can include a solid plate directed toward the patient's chest of the patient 2, this plate being forced against the chest when the compartment is filled.

The disclosed embodiments can be combined where appropriate. For instance, the bellows system 12 shown in the first embodiment can be used in the arc 10B shown in the second embodiment. The pressure can be obtained by gravity acting on a weight, pneumatic means, hydraulic means, mechanical means or any other suitable pressure generating means.

Although the patient has been shown to be in a supine position in all embodiments, other positions are possible, as long as the chest is accessible for the apparatus.

Although modifications and changes may be suggested by those skilled in the art, it is the intention of the inventor to embody within the patent warranted hereon all changes and modifications as reasonably and properly come within the scope of his contribution to the art.

I claim as my invention:

1. A respiratory apparatus comprising:
   a breathing-assist apparatus adapted for connection via a tubing system to airways of a subject for supplying respiratory gas to a patient within a respiratory cycle; and
   an extracorporeal arrangement adapted for mechanical extracorporeal contact with a patient to direct a controllable pressure to at least one selected position on a thorax of a patient, synchronized with the supply of gas from said breathing assist apparatus, to promote distribution of said gas in the lungs of a patient.

2. A respiratory apparatus as claimed in claim 1 wherein said extracorporeal arrangement includes means for controlling and varying said pressure according to a predetermined pattern in at least one respiration cycle.

3. A respiratory apparatus as claimed in claim 1 wherein said extracorporeal arrangement comprises:
   a support adapted for mounting above a patient; and
   at least one mechanical pressure–applying actuator connected to said support and adapted for extracorporeal contact with a patient at said at least one selected position for applying said pressure.

4. A respiratory apparatus as claimed in claim 3 wherein said support comprises an arc spanning a patient from side-to-side.

5. A respiratory apparatus as claimed in claim 3 wherein said support comprises an arm adapted for attachment at a head end of a patient bed, and projecting over a head and thorax of a patient.

6. A respiratory apparatus as claimed in claim 3 wherein said mechanical actuator comprises a weight suspended from to said support.

7. A respiratory apparatus as claimed in claim 3 wherein said mechanical actuator comprises an expandable element connected to said support.

8. A respiratory apparatus as claimed in claim 1 wherein said extracorporeal arrangement comprises an inflexible cover adapted to be secured across a thorax and including a plurality of selectively pressurizable compartments for directing said pressure to said at least one selected position.

9. A respiratory apparatus as claimed in claim 8 wherein said cover comprises a vest adapted to be worn by a patient.

10. A respiratory apparatus as claimed in claim 8 wherein said extracorporeal arrangement further comprises a source of pressurized fluid connected to said compartments, and means for, controlling supply of said fluid individually to each compartment.

11. A respiratory apparatus as claimed in claim 1 wherein said extracorporeal arrangement comprises:
    a pressure-applying element adapted for mechanical contact at a selected position on a thorax of a patient;
    a force generating unit; and
    a force directing element connected between said force generating unit and said force applying element for selectively varying and directing said force generated by said force generating unit to said force applying element.

* * * * *